US012681005B2

(12) United States Patent
Gao et al.

(10) Patent No.: US 12,681,005 B2
(45) Date of Patent: Jul. 14, 2026

(54) ELECTROCHEMICAL SENSING APPROACH FOR MOLECULE QUANTIFICATION IN BODY FLUIDS

(71) Applicant: California Institute of Technology, Pasadena, CA (US)

(72) Inventors: Wei Gao, Pasadena, CA (US); Minqiang Wang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 626 days.

(21) Appl. No.: 18/078,015

(22) Filed: Dec. 8, 2022

(65) Prior Publication Data

US 2023/0105411 A1 Apr. 6, 2023

Related U.S. Application Data

(62) Division of application No. 16/803,838, filed on Feb. 27, 2020, now Pat. No. 11,549,934.

(Continued)

(51) Int. Cl.
*G01N 33/487* (2006.01)
*B01L 3/00* (2006.01)
*G01N 27/02* (2006.01)

(52) U.S. Cl.
CPC .......... *G01N 33/48707* (2013.01); *B01L 3/50* (2013.01); *G01N 27/02* (2013.01); *B01L 2300/0645* (2013.01); *B01L 2300/12* (2013.01)

(58) Field of Classification Search
CPC .............. G01N 27/02; G01N 27/3275; G01N 33/48707; G01N 33/5438; G01N 2600/00;

(Continued)

(56) References Cited

U.S. PATENT DOCUMENTS

2001/0017269 A1 8/2001 Heber
2010/0300899 A1 12/2010 Levin
(Continued)

FOREIGN PATENT DOCUMENTS

CN 101666774 A 3/2010
CN 104569094 A 4/2015
(Continued)

OTHER PUBLICATIONS

Manickam, Pandiaraj, et al. "A reusable electrochemical biosensor for monitoring of small molecules (cortisol) using molecularly imprinted polymers." Journal of the Electrochemical Society 164.2 (2016): B54. (Year: 2016).*

(Continued)

*Primary Examiner* — Robert J Eom
(74) *Attorney, Agent, or Firm* — Sheppard Mullin Richter & Hampton LLP

(57) ABSTRACT

A portable biosensor for detecting and quantifying a target molecule in a biological sample and method of use include a biosensor fabricated with a recognition layer with an imprinted polymer, an electrode electrically coupled to the recognition layer, and a logic circuit that may include a processor and non-transitory memory with computer executable instructions embedded thereon, wherein the imprinted polymer is shaped to have a profile that substantially matches a profile of the target molecule, such that the target molecule can form-fit and bind to the imprinted polymer, thus changing an electrical property of the polymer layer that may be detected to identify the presence of the target molecule.

20 Claims, 9 Drawing Sheets

Related U.S. Application Data

(60) Provisional application No. 62/811,177, filed on Feb. 27, 2019.

(58) Field of Classification Search
CPC . B01L 3/50; B01L 2300/0645; B01L 2300/12
See application file for complete search history.

(56) References Cited

U.S. PATENT DOCUMENTS

| 2011/0139636 | A1 | 6/2011 | Lai et al. | |
|---|---|---|---|---|
| 2016/0178649 | A1 | 6/2016 | Shashidhar et al. | |
| 2016/0377611 | A1* | 12/2016 | Ma | G01N 33/5438 |
| | | | | 422/69 |
| 2017/0227486 | A1 | 8/2017 | Bhansali et al. | |
| 2018/0230524 | A1 | 8/2018 | Honarvar Nazari et al. | |

FOREIGN PATENT DOCUMENTS

| CN | 106841343 | A | 6/2017 |
|---|---|---|---|
| WO | 2016/140337 | A1 | 9/2016 |
| WO | 2016/190727 | A1 | 12/2016 |
| WO | 2017/222724 | A1 | 12/2017 |
| WO | 2018/031497 | A1 | 2/2018 |

OTHER PUBLICATIONS

Panasyuk, Tatiana L., et al. "Electropolymerized molecularly imprinted polymers as receptor layers in capacitive chemical sensors." Analytical Chemistry 71.20 (1999): 4609-4613. (Year: 1999).*

Second Office Action dated Oct. 17, 2024, issued in related Chinese Patent Application No. 202080016613.8, with English machine translation (41 pages).

Xiuchun Guo et al., "Molecularly Imprinted Polymer-Based Electrochemical Sensors", Chemical Research, vol. 27, No. 1, Dec. 31, 2016, p. 1-11, with English language abstract.

Examination Report dated May 14, 2024, issued in related European Patent Application No. 20762664.9 (7 pages).

Extended European Search Report dated Oct. 18, 2022, issued in related European Application No. 20762664.9 (8 pages).

Examination Report dated Sep. 1, 2023, issued in related European Application No. 20762664.9 (6 pages).

A. Diouf et al., "An electrochemical biosensor based on molecularly imprinted polymer for the quanitifcation of creatinine in human urine samples," 2017 ISOCS/IEEE International Symposium on Olfaction and Electronic Noise (ISOEN), IEEE, May 28, 2017.

Yunlong Dai et al., "Voltametric determination of paracetamol using a glassy carbon electrode modified with Prussian Blue and a molecularly imprinted polymer, and ratiometric read-out of two signals," Microchimica Acta, Springer Vienna, Vienna, vol. 183, No. 10, Aug. 9, 2016, pp. 2771-2778.

Hui-Chi Huang et al., "A multi-array sensor via the integration of acrylic molecularly imprinted photoresists and ultramicroelectrodes on a glass chip," Analytica Chimica Acta, Elsevier, Amsterdam, NL, vol. 582, No. 1, Jan. 16, 2007, pp. 137-146.

Suzhu Yu et al., "Effect of Porogenic Solvent on the Porous Properties of Polymer Monoliths", Journal of Applied Polymer Science, May 16, 2012, pp. 2041-2047.

Xingliang Song et al., "Effect of Porogenic Solvent on Selective Performance of Molecularly Imprinted Polymer for Quercetin", Materials Research, vol. 12, No. 3, 2009, pp. 299-304.

Mohamed H. Mohamed et al., "Porous Copolymer Resins: Tuning Pore Structure and Surface Area with Non Reactive Porogens", Nanomaterials, 2, 2012, pp. 163-186.

Aftim et al., "Biosensor-assisted selection of optimal parameters for designing molecularity imprinted polymers selective to phosmet insecticide", Talanta, 2017, vol. 174, pp. 414-419.

International Preliminary Report on Patentability for Application No. PCT/US2020/020203, mailed on Aug. 25, 2021, 7 pages.

International Search Report and Written Opinion for Application No. PCT/US2020/020203, mailed on Jun. 30, 2020, 8 pages.

Third Office Action dated May 6, 2025, issued in Chinese Patent Application No. 202080016613.8, with English machine translation (55 pages).

Zeng Rong et al, "Biomedical Bionic Polymer Materials," South China University of Technology Press, Oct. 31, 2010, pp. 64-70, with English machine translation.

Final Rejection Decision dated Jul. 28, 2025, issued in Chinese Patent Application No. 202080016613.8, with English machine translation (49 pages).

* cited by examiner 401     402     403

404     405     406

601

602

603

604

800

810   Introduce The Biological Sample To The Biosensor

820   Obtain A Measurement Of The Electrical Property

830   Generate An Indication Based On The Measurement

840   Display The Indication

ELECTROCHEMICAL SENSING APPROACH FOR MOLECULE QUANTIFICATION IN BODY FLUIDS

CROSS-REFERENCE TO RELATED APPLICATIONS

This application is a divisional of U.S. patent application Ser. No. 16/803,838, filed Feb. 27, 2020, which claims priority to U.S. provisional application No. 62/811,177, filed Feb. 27, 2019, the contents of which are incorporated herein by reference in their entireties.

BACKGROUND

The concentration of a drug in an organism is regulated by the amount of drug ingested and/or consumed by the organism over time (dose) and the rate at which the drug is metabolized and eliminated from the organism. A drug may be metabolized by the organism and broken down into chemical components or may be excreted from the organism in a substantially unaltered form depending on the chemical composition of the drug. Excretion may occur through various mechanisms, including excretion through sweat, blood, urine, saliva, exhaled air, or other excretion processes. For example, in the context of human subjects, excreted drugs can be monitored to track the subject's compliance to prescriptions and tailor their dosage to achieve optimal benefits, and/or to detect and measure the use of illicit and/or unprescribed medication. Monitoring excreted drugs can also assist in the analysis of complex pharmacokinetics of certain drugs, and help with forensic investigation in certain law enforcement, medical, and/or research cases.

Traditional analytical methods for monitoring various drugs in biological excretions include high performance liquid chromatography (HPLC), liquid chromatography-tandem mass spectrometry (LC-MS/MS), capillary electrophoresis-mass spectrometry (CE-MS), enzyme-linked immunosorbent assay (ELISA), among others. Although these methods are highly sensitive and accurate, they require large, expensive equipment and employ complicated sample purification and analysis procedures making mobile real-time detection difficult. Accordingly, there is a need for a more accurate, mobile, and cost-effective method for detecting and quantifying molecular compounds in various biological samples.

SUMMARY

The technology disclosed herein is directed to detecting and quantifying molecular compounds in biological specimens. The wearable and/or portable biosensor and methods disclosed herein enable the efficient, cost-effective, and accurate detection and quantification of a target molecule in a biological sample in a manner that is not constrained by geographic location or facility capabilities. For example, the biological sample may include blood, sweat, saliva, urine, or other substance excreted from an organism. In some examples, the organism could be a human or animal.

In an example embodiment of the disclosed technology, a biosensor for detecting a target molecule in a biological sample includes a recognition layer with an imprinted polymer, an electrode electrically coupled to the recognition layer, and a logic circuit with a processor and a non-transitory memory with computer executable instructions embedded thereon. For example, a target molecule may include a specific protein, peptide, vitamin, amino acid, hormone, or drug metabolite. In some examples, a recognition layer may include an imprinted polymer that is shaped to have a profile that substantially matches a profile of the target molecule, such that the target molecule can form-fit and bind to the imprinted polymer. The electrode, for example, may be configured to detect a measurement of an electrical property of the recognition layer. In embodiments, the logic circuit may be electrically coupled to the electrode and the computer executable instructions may cause the processor to identify the electrical property detected with the electrode when the target molecule binds to the imprinted polymer.

In some embodiments, the recognition layer of the biosensor may be regenerated in-situ. In some embodiments, the recognition layer may be arranged into an array having multiple rows, wherein each of the rows may have an imprinted polymer that is independently electrically coupled to an electrode. For example, the array may be used to detect the presence of more than target molecule at a time.

In embodiments, the electrical property may be an electrical current, an electrical voltage, or an electrical impedance. In some embodiments, the biosensor may also include uniform redox probe, wherein the uniform redox probe is deposited on a surface of the electrode. In some embodiments, the electrode may include a catalytically active substrate.

In some embodiments, the computer executable instructions may include causing the processor to generate an indication identifying the presence of the target molecule based on the electrical property of the recognition layer detected with the electrode.

In some embodiments, the biosensor also may include a display, wherein the computer executable instructions may also cause the processor to output the indication identifying the presence of the target molecule to the display.

In an example of the embodiments, a method for detecting a target molecule in a biological sample using a biosensor is disclosed. The biosensor, for example, may include a recognition layer with at least one imprinted polymer, with the imprinted polymer being shaped to have a profile that substantially matches a profile of the target molecule, an electrode electrically coupled to the recognition layer, and a logic circuit. The method, for example, may include introducing the biological sample to the biosensor, wherein the target molecule will form-fit and bind to the imprinted polymer when the target molecule is present in the biological sample. In some embodiments, the method may also include obtaining, with the electrode, a measurement of an electrical property of the recognition layer. In some embodiments, the method may also include generating, with the logic circuit, an indication that the target molecule is present in the biological sample based on the measurement of the electrical property.

In some embodiments, the method may also include sweeping the electrode to regenerate the recognition layer in situ. In some embodiments, the method may also include depositing a uniform redox probe on a surface of the electrode.

In some embodiments, the electrical property may include an electrical current, an electrical property, and/or an electrical impedance.

In some embodiments, the target molecule may include an electroactive molecule. For example, the electroactive target molecule may include tryptophan, tyrosine, phenylalanine, dopamine, vitamin C, vitamin B6, vitamin B12, uric acid, mycophenolic acid, caffeine, methionine, cortisol, noradrenaline, or adrenaline.

In some embodiments, the target molecule further may include a non-electroactive molecule. For example, the non-electroactive target molecule may include leucine, isoleucine, valine, busulfan, cyclophosphamide, creatinine, or urea.

In some embodiments, a method for detecting a target molecule in a biological sample using a biosensor is disclosed. For example, the biosensor may include a recognition layer with at least one imprinted polymer, the imprinted polymer being shaped to have a profile that substantially matches a profile of the target molecule. The biosensor may also include an electrode electrically coupled to the polymer layer and having at least one surface with an uniform redox probe. In some embodiments, the biosensor also may include a logic circuit and a display. In some embodiments, the method may include introducing the biological sample to the biosensor, wherein the target molecule will form-fit and bind to the imprinted polymer when the target molecule is present in the biological sample; obtaining, with the electrode, a measurement of an electrical property of the recognition layer upon the target molecule binding to the imprinted polymer. In some embodiments, the method may also include generating, with the logic circuit, an indication that the target molecule is present in the biological sample based on the measurement of the electrical property. In some embodiments, the method may also include causing the display to display the indication identifying the presence of the target molecule.

In some embodiments, the method may also include sweeping the electrode to regenerate the recognition layer in-situ. In some embodiments, the uniform redox probe may include ferric ferrocyanide.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

Analytical methods for detecting molecules in a biological sample may include high performance liquid chromatography (HPLC), liquid chromatography-tandem mass spectrometry (LC-MS/MS), capillary electrophoresis-mass spectrometry (CE-MS), enzyme-linked immunosorbent assay (ELISA), among others. Although these methods are highly accurate, they are carried out on large expensive machines that require technical skill to operate. Moreover, because these methods require large and difficult machines to perform the analysis, they are not easily deployable to specific locations for the rapid and accurate analysis of a biological sample.

Molecular imprinting is an emerging method that uses in-situ polymerization to produce synthetic antibodies (i.e., biomimetic recognition sites) possessing high substrate selectivity and specificity. Functional monomers, cross-linkers, and template molecules are combined and polymerized creating a synthesized polymer layer or matrix. Once the template molecule is removed, the remaining polymer layer contains recognition sites that can accurately identify the original template molecule. Molecular imprinting technology may be used to monitor both electroactive and non-electroactive target molecules (e.g., drugs, amino acids, vitamins, hormones, etc.), and because of its low-cost and accuracy, provides a cost-effective alternative to the aforementioned analytical methods.

Although promising, molecular imprinting technology remains a seldom-used analytical method for rapid on-site analysis of molecular compounds in biological specimens. To address the deficiencies of present molecular compound analytical systems and methods, the technology disclosed herein is directed to a portable and/or wearable biosensor that allows for the rapid and cost-effective analysis of molecules in a biological sample at any location.

Figure 1:
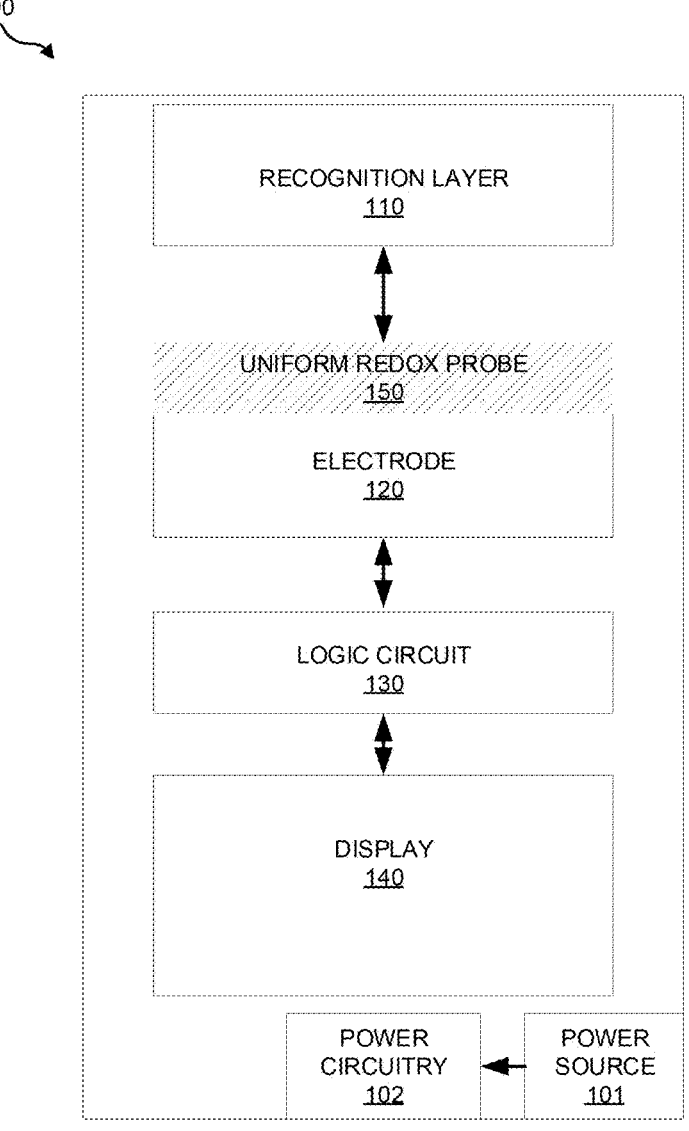
FIG. 1 is a block diagram illustrating some components of a portable biosensor, in accordance with various embodiments of the disclosure.

FIG. 1 is a block diagram illustrating some components of biosensor 100, in accordance with various embodiments of the disclosure. The biosensor 100 may include, for example, a recognition layer 110 comprising an imprinted polymer, as electrode 120, a logic circuit 130, and optionally, a display 140 and a uniform redox probe 150. The electrical components of biosensor 100 may be powered by a power source 101 that connects to power circuitry 102 for distributing power. The power source 101 may be a battery, capacitor, or other power source known in the art. The power source 101 may be rechargeable (e.g., via a USB port and/or an AC/DC converter), and it should be appreciated that any suitable power source technologies may be used to power the components of biosensor 100. For example, lithium-ion batteries, cell batteries, piezo or vibration energy harvesters, photovoltaic cells, AC/DC sources, or other like devices can be used.

During operation, biosensor 100 may be introduced to a biological sample containing a target molecule. Upon the successful binding of the target molecule to an imprinted polymer of recognition layer 110, electrode 120 detects a measurement of an electrical property of the recognition layer 110 and logic circuit 130 generates an indication that the target molecule is present in the biological sample. In embodiments, biosensor 100 may also include a display 140 to display the indication. In some embodiments, biosensor 100 may also include a redox probe 150 that is deposited on a surface of the electrode.

In various embodiments, recognition layer 110 may include an imprinted polymer. An "imprinted polymer," as referred to herein, is a polymer that is shaped to have a profile that substantially matches the profile of a target molecule, such that the target molecule can form-fit and bind to the imprinted polymer. In embodiments, an imprinted polymer may be synthesized by combining functional monomers with template molecules and cross-linkers in a porogenic solvent. The functional monomers interact with the template molecules and become fixed in place once polymerized. Following polymerization, the solvent and template molecules are removed leaving behind a recognition layer comprising an imprinted polymer that may bind specifically to the template molecule. In some embodiments, the recognition layer including the imprinted polymer may be broken down into individually imprinted monomers. Breakdown can be achieved mechanically, for example, by using sonication or mortar and pestle. In some embodiments, breakdown can be achieved chemically, for example, by applying acid and other dissolving agents. In some embodiments, recognition layer 110 may include at least one imprinted polymer. In some embodiments, recognition layer 110 may include more than one imprinted polymers. In some embodiments, recognition layer 110 may include a plurality of imprinted monomers. In some embodiments, recognition layer 110 may include at least one imprinted monomer.

In various embodiments, recognition layer 110 may include differently imprinted polymers. For example, recognition layer 110 may include an array having multiple rows, wherein the imprinted polymers within a row recognize and bind a different target molecule. In some embodiments, recognition layer 110 may include an array, wherein each imprinted polymer can recognize and bind different target molecules. In some embodiments, recognition layer 110 may include an array having a plurality of imprinted monomers, wherein each of the imprinted monomers can recognize and bind a different target molecule. In embodiments, recognition layer 110 may be arranged into an array having more than one imprinted polymers, wherein each imprinted polymer is electrically coupled to an electrode.

Different functional monomers may be used when synthesizing the imprinted polymer. When choosing a functional monomer, factors such as the charge of the template molecule may be considered. For example, template molecules that are pronated may require a more acidic functional monomer as to not disrupt the charge of the template target. Moreover, additional factors such as the ratios of functional monomer to cross-linker and functional monomer to template molecule may also be considered when synthesizing the imprinted polymer. Titrating these factors to achieve a good interaction between functional monomer and template molecule is essential to the specificity of the imprinted polymer. Because recognition layer 110 must be thin enough to successfully transduce binding events, the functional monomer employed must be both insulating and thin. In embodiments, the functional monomer may include, for example, phenol or polyphenol. In some embodiments, the functional monomer may include, for example, pyrene (polypyrene) or a pyrene derivative such as naphthalene, phenanthrene, or perylene. In some embodiments, the functional monomer may comprise aniline (polyaniline), pyrrole (polypyrrole), thiophene, and/or carbazole. It is to be understood that one of ordinary skill in the art would know how to choose the correct functional monomers, cross-linkers, and template molecules, including workable ratios of each, to prepare a polymer.

Figure 2:
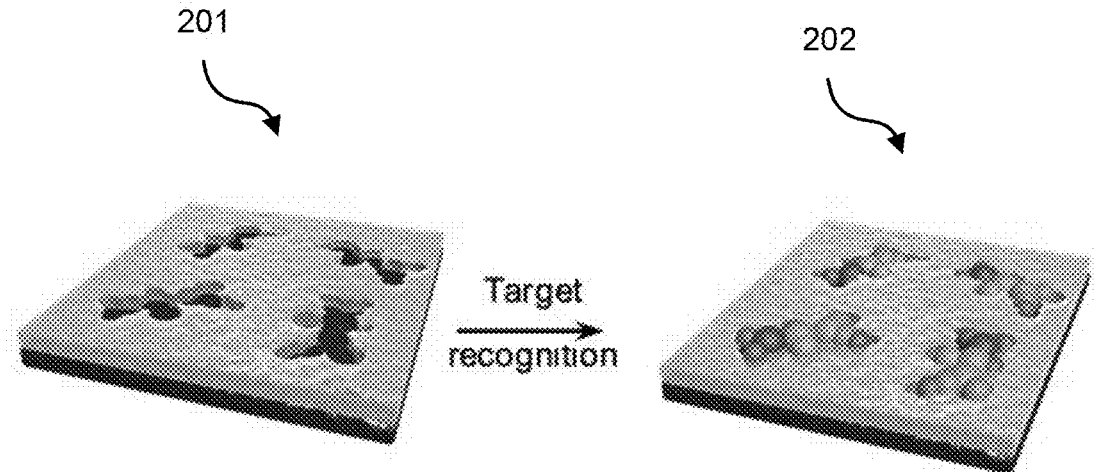
FIG. 2 illustrates an example target molecule recognition in accordance with various embodiments of the disclosure.

FIG. 2 illustrates an example recognition layer as used in accordance with various embodiments disclosed herein. Imprinted layer 201, for example, may include an imprinted polymer configured to recognize and accept a target molecule within a biological sample. Target-bound polymer layer 202 illustrates by way of example, a target molecule form-fitting into the imprinted polymer in accordance with the various embodiments disclosed herein.

Referring again to FIG. 1, biosensor 100 may also include an electrode 120. Electrode 120 is electrically coupled to recognition layer 110 and is configured to detect a measurement of an electrical property of recognition layer 110. In embodiments, electrode 120 may include a catalytically active substrate. Several types of electrode materials may be used in accordance with the embodiments disclosed herein. Each electrode material has its own advantages and disadvantages. Traditional electrode materials include, for example, graphite, platinum, gold, rhodium, indium, tin, copper, zinc, lead, and/or silver. More contemporary electrode materials include, for example, metallic nanowires, carbon nanotubes (CNTs), conductive polymers, and graphene (including graphene film). Graphene, for example, represents a promising conducting material and may be used as an electrode in a number of different applications including in transistors, light-emitting diodes, liquid crystal displays, molecular junction devices, touch screens, solar cells, and flexible devices. Graphene's advantages include its high charge mobility, transparency, mechanical strength, and flexibility. In embodiments, electrode 120 may include a catalytically active substrate, for example, graphene. In some embodiments, electrode 120 may include a graphite, platinum, gold, rhodium, indium, tin, copper, zinc, lead, and/or silver electrode. In some embodiments, other conductive materials may be used to form electrode 120, including for example, metallic nanowires, carbon nanotubes (CNTs), and/or conductive polymers. Such nanomaterials may also be used to increase the surface area and/or the signal response of the electrode.

As depicted in FIG. 1, electrode 120 is coupled to recognition layer 110 and may be configured to detect a measurement of an electrical property of recognition layer 110. In embodiments, a measurement of an electrical property may become detectable by electrode 120 upon binding of a target molecule to the imprinted polymer of recognition layer 110. In embodiments, the electrical property may include an electrical current. In some embodiments, the electrical property may include an electrical voltage. In some embodiments, the electrical property may include an electrical impedance. In embodiments, electrode 120 may be coupled to recognition layer 110 and may be configured to detect a measurement of an electrical property. In embodiments, a measurement of an electrical property may include reaching or meeting a threshold of an electrical property. In some embodiments, a measurement of an electrical property may include reaching or meeting a threshold on an electrical property such that when the threshold is reached or met, the measurement may be recorded and sent to the logic circuit for processing. In embodiments, a measurement may include a change in the electrical property. In some embodiments, a measurement may include a change in the electrical property such that when the change in electrical property may be detected, for example, from a baseline, the measurement may be sent to the logic circuit for processing. In some embodiments, a change in electrical property may include an increase or decrease in the electrical property from a certain baseline. In some embodiments, the change in the electrical current, electrical voltage, or electrical impedance, may include a change from a baseline level, or between two or more readings, depending on the assay performed.

Recognition layer 110 may be coupled to electrode 120 in accordance with various embodiments disclosed herein. Various methods may be used to couple recognition layer 110 to electrode 120, including, but not limited to, electropolymerization methods (i.e., electrochemical polymerization methods), chemical methods, and/or self-assembly coupling methods. All of these methods generally entail, for example, formation of the polymer layer and depositing of the polymer layer onto the conducting substrate. Different advantages and disadvantages apply to each. In embodiments, electropolymerization may be used to couple recognition layer 110 to electrode 120. In embodiments, a potential may be applied high enough to oxidize the functional monomers and achieve polymerization, but low enough as to not dissolve the substrate/electrode. In embodiments, electropolymerization may be performed using an electrochemical cell. In some embodiments, electropolymerization may be performed using a three electrode system. In embodiments, electropolymerization may include oxidation of a functional monomer by applying, for example, a constant current (galvanostatic), a constant potential (potentiostatic), or a sweeping potential (potentiodynamic).

In embodiments, electropolymerization may include attracting recognition layer 110 onto the surface of the electrode 120 in a three electrode system, wherein recognition layer 110 may include an imprinted polymer with at least one imprinted monomer, and wherein electrode 120 may include a graphene substrate. In some embodiments, once recognition layer 110 is attracted to electrode 120, application of a current using cyclic voltammetry couples the imprinted polymers to the electrode creating a thin, uniform layer through which a binding event may be detected. Other coupling methods may also be used to electrically couple recognition layer 110 to electrode 120 including electropolymerization methods, self-assembly polymerization methods, and chemical polymerization methods.

In embodiments, electrode 120 may be swept to regenerate the imprinted polymer of recognition layer 110 in-situ. In embodiments, sweeping of electrode 120 may comprise rapid voltammetric and/or amperometric sweeping of the electrode in order to dissociate the bound target molecules from the imprinted polymer such that the recognition layer may be regenerated. In some embodiments, regeneration of the recognition layer 110 allows for the continuous use of imprinted polymer of recognition layer 110, and therefore, the reusability of biosensor 100. As used in accordance to several embodiments of the disclosure, "regeneration" or "regenerated" may include the release of the target molecule and/or the template molecule from an imprinted polymer, such that the imprinted polymer is able to bind a target molecule.

Referring still to FIG. 1, biosensor 100 may also include a logic circuit 130. In embodiments, logic circuit 130 may be electrically coupled to electrode 120 and may include a processor and a non-transitory memory with computer executable instructions embedded thereon. In various embodiments, logic circuit 130 may also include other circuits receiving, processing, and/or storing content, data, and other information. Logic circuit 130 may also, for example, facilitate the receipt of such content, data, or other information, as well as the generation of such content, data, or other information by the biosensor 100.

In embodiments, the computer executable instructions embedded within logic circuit 130 cause the processor to identify the electrical property of polymer layer 110 when the target molecule binds to the imprinted monomer. In some embodiments, the computer executable instructions embedded within logic circuit 130 cause the processor to generate an indication identifying the presence of the target molecule based on the electrical property of the polymer layer. In embodiments, the indication may be transmitted electrically to a display to be identified visually. In some embodiments, the indication may be transmitted electrically to a an LED, or a plurality of LEDs, to be identified visually. In embodiments, the indication generated may be stored on the non-transitory memory of logic circuit 130.

Biosensor 100 may include a display 140. In embodiments, display 140 displays the presence of a target molecule and may be electrically coupled to logic circuit 130. In some embodiments, upon the binding of a target molecule, the computer executable instructions cause the processor generate and output an indication identifying the presence of the target molecule to display 140. Non-limiting examples of display 140 include: a liquid-crystal display (LCD); an organic LCD (OLCD); a light emitting diode display (LED); an organic light emitting diode display (OLED); digital light processing display (DLP); among others.

In various embodiments, biosensor 100 may also include a uniform redox probe 150. Uniform redox probe 150 may be used according to various embodiments disclosed herein to detect both electroactive and non-electroactive target molecules. Unlike electroactive target molecules, non-electroactive target molecules do not transfer their electrons (i.e., do not become oxidized) upon binding to an imprinted polymer coupled to an electrode. Uniform redox probe 150 may be used to detect both electroactive and non-electroactive molecules indirectly through loss of current as a result of their binding at the imprinted polymer coupled to electrode 120. In some embodiments, the uniform redox probe 150 may be deposited on a surface of electrode 120. In some embodiments, uniform redox probe may be incorporated into the matrix of recognition layer 110. In embodiments, uniform redox probe 150 may be electrically coupled between recognition layer 110 and electrode 120. In some embodiments, the uniform redox probe 150 may include ferric ferrocyanide (e.g., Prussian Blue). Uniform redox probe 150 may include, for example, thionine; anthraquinone 2-carboxylic acid; ferrocenecarboxylic acid; tris(2,2'-bipyridine-4,4'-dicarboxylic acid)cobalt(III); among others.

The biosensor 100 of FIG. 1 may be used to detect a target molecule in a biological sample. In embodiments, a biological sample may include an excreted bodily fluid, such as, for example, sweat, urine, tears, blood, salvia, and secretions from the male and female sex organs. Target molecules may include proteins, electrolytes, vitamins, amino acids, metabolized drugs, among other molecules and/or compounds. In some embodiments, a target molecule may include an electroactive molecule. Electroactive molecules may include, for example, tryptophan, tyrosine, phenylalanine, dopamine, vitamin C, vitamin B6, vitamin B12, uric acid, mycophenolic acid, caffeine, methionine, cortisol, noradrenaline, or adrenaline. In embodiments, a target molecule may comprise a non-electroactive molecule. Non-electroactive molecules may include, for example, leucine, iso-leucine, valine, busulfan, cyclophosphamide, creatinine, or urea. The lists of electroactive and non-electroactive molecules is not meant to be exhaustive. It is to be understood that additional electroactive/non-electroactive molecules not listed here, may also be detected according to the various systems and methods disclosed herein.

In various embodiments, a target molecule may include an amino acid. Amino acids that may be detected using embodiments of the disclosure include: alanine; glycine; isoleucine; leucine; proline; valine; phenylalanine; tryptophan; tyrosine; aspartic acid; glutamic acid; arginine; histidine; lysine; serine; threonine; cysteine; methionine; asparagine; and glutamine. In various embodiments, a target molecule may include a vitamin or provitamin (i.e., vitamin precursors). For example, vitamins and provitamins that may be detected include: thiamine (vitamin B1); riboflavin (vitamin B2); niacin (vitamin B3); choline (vitamin B4); pantothenic acid (vitamin B5); pyridoxine (vitamin B6); biotin (vitamin H, vitamin B7, or vitamin B8); folic acid (vitamin B9 or folate); and cobalamin (vitamin B12); ascorbic acid (vitamin C); retinol (vitamin A); calciferol (vitamin D); tocopherol (vitamin E); phylloquinone (vitamin K1); menaquinone (vitamin K2); β-carotin (vitamin A); 7-dehydrocholesterol (vitamin D); and cholecalciferol (vitamin D).

In various embodiments, the target molecule may include, for example, a hormone. Hormones that may be detected include: cholesterol; cortisol; progesterone; testosterone; corticosterone; aldosterone; β-estradiol; insulin; estrogen; thyroxin; gonadotropin-releasing hormone (GnRH); corticotropin-releasing hormone; melatonin; human growth hormone (HGH); adrenocorticotropic hormone; prolactin; and angiotensin. In some embodiments, a target molecule may include a protein used for diagnosis purposes, including for detecting and monitoring various illnesses (e.g., cancer). For example, a target molecule may include tumor markers for detecting and monitoring cancer, including: serum carcinoembryonic antigen (CEA); serum lipid-associated sialic acid (LASA); serum cancer antigen 19-9 (CA 19-9); cancer antigen 125 (CA 125); alpha fetoprotein (AFP); lactase dehydrogenase (LDH); and human chorionic gonadotropin (hCG). The list of target molecules is not meant to be exhaustive. It is to be understood that additional target molecules not listed here, may also be detected according to the various systems and methods disclosed herein.

Figure 3:
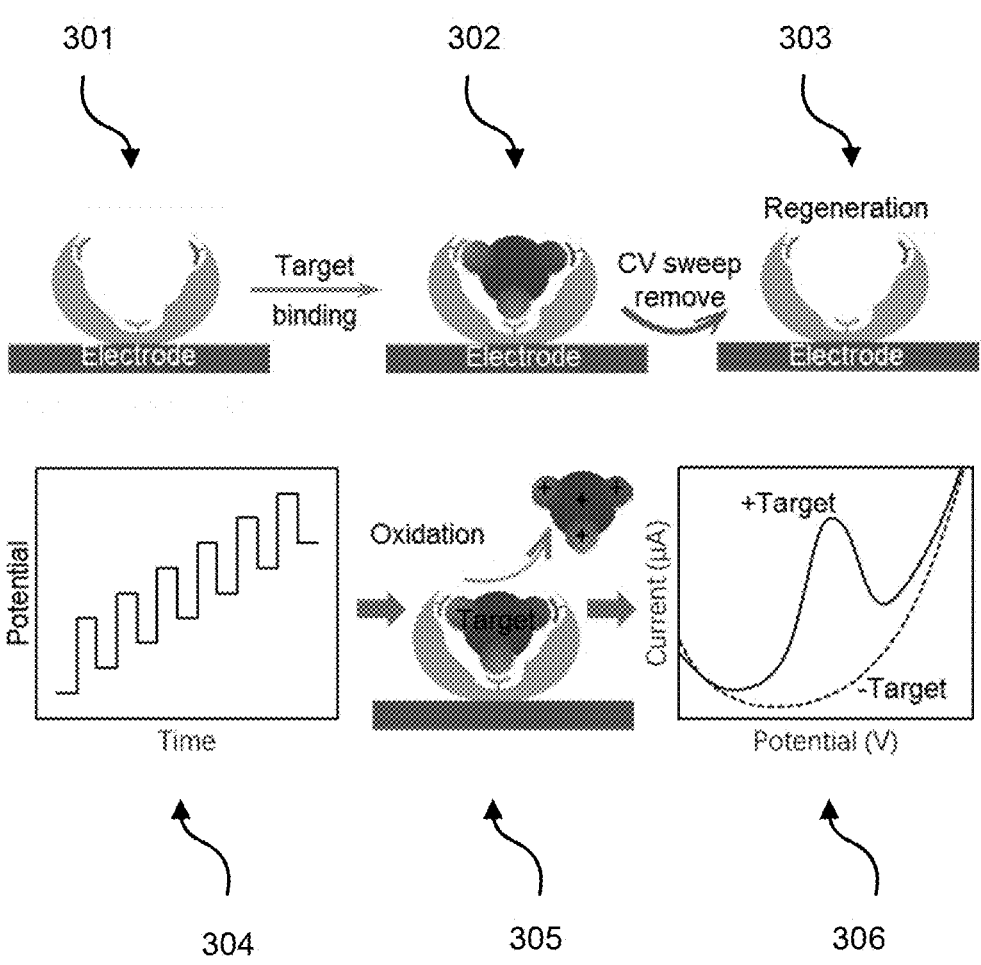
FIG. 3 illustrates, by way of example, the binding of a target molecule and generation of an indication, in accordance with various embodiments of the disclosure.

FIG. 3 depicts detection and quantification approach for an electroactive target molecule, by way of example, based on various embodiments of the disclosure. Polymerization of functional monomers, cross-linkers and template molecules under an electrical current forms a recognition layer, capable of specifically recognizing and binding a target molecule. Frame 301 depicts a recognition layer coupled to an electrode, which may include, by way of example, graphene. The individual form-fitting sites that comprise the imprinted polymer of the recognition layer are shown. Frame 302 depicts binding of a template molecule to the imprinted polymer of the recognition layer. Frame 303 depicts regeneration of recognition layer, following removal of the template molecule. In embodiments, regeneration of the recognition layer may be achieved by rapid voltammetric sweeping of the electrode, or through use of other solutions including, for example, strong acids and/or organic solvents.

Frames 304 and 305 depict detection of a target molecule using, by way of example, differential pulse voltammetry (DPV). As seen in frame 304, the binding of a target molecule to an imprinted polymer of the recognition layer increases the potential (or voltage) detected by the sensor over time. In embodiments, detection of a target molecule using DPV may include use of a three-electrode system comprising a sensing electrode comprising, imprinted polymers coupled to a graphene substrate; a working electrode comprising, for example, gold, platinum, carbon, or mercury; and a counter electrode. Frame 305 depicts oxidation of the target molecule, whereby the electrolytes of the bound electroactive target molecule transfer to the electrode creating a measurement of an electrical property. This measurement may be detected by the electrode. Frame 306 depicts the graphical representation, or an indication, of the quantity of target molecule bound. In embodiments, upon a target molecules binding and detection by the electrode, the computer executable instructions embedded on the logic circuit cause the processor to identify the electrical property detected with the electrode. In some embodiments, the computer executable instructions further cause the processor to output the indication identifying the presence of the target molecule to the display.

Figure 4:
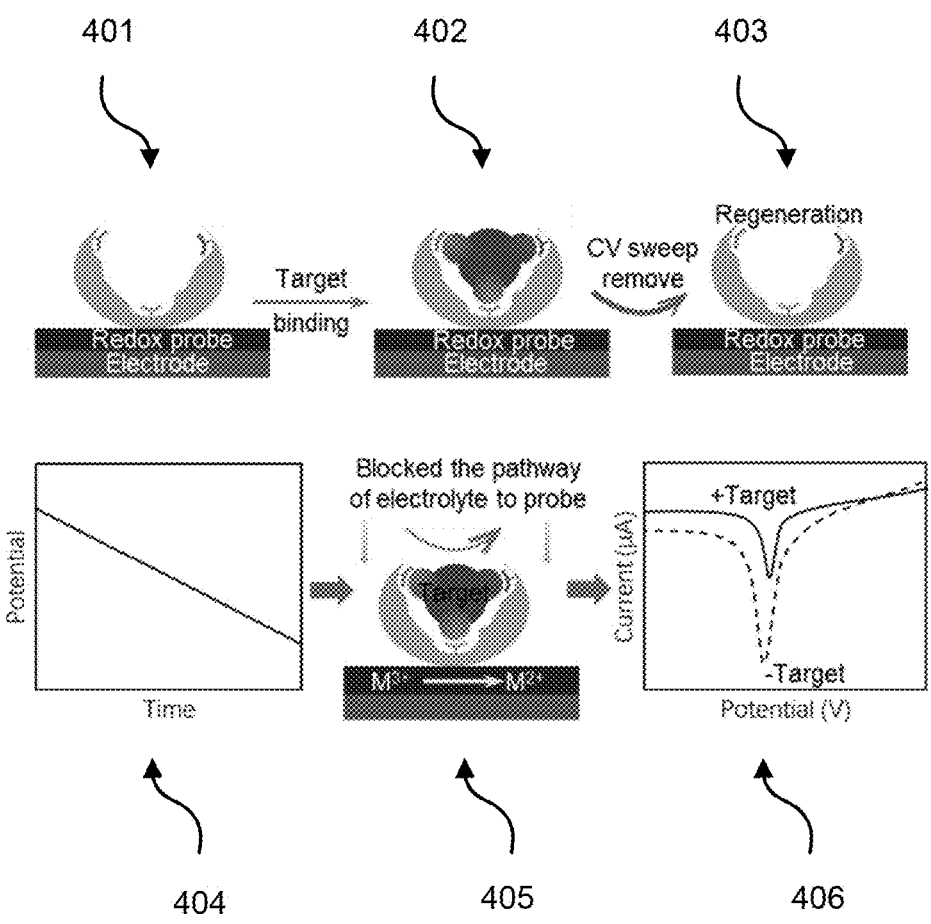
FIG. 4 illustrates, by way of example, the binding of a target molecule and generation of an indication, in accordance with various embodiments of the disclosure.

FIG. 4 depicts a detection and quantification approach for non-electroactive target molecules in accordance with various embodiments of the disclosure. Frames 401-403 depict the formation of a recognition layer capable of specifically recognizing and binding a target molecule. When detecting a non-electroactive molecule, a uniform redox probe may be deposited onto a surface of the electrode such that it is between the recognition layer and the electrode. In embodiments, the redox probe may include ferric ferrocyanide (e.g., Prussian Blue), for example. Other uniform redox probes may also be used including thionine and anthraquinone 2-carboxylic acid. In embodiments, the uniform redox probe may be electrically coupled between the recognition layer and the electrode. In some embodiments, the uniform redox probe may be embedded within the matrix of the recognition layer. In some embodiments, the uniform redox probe may be in the working solution. Frame 404 depicts the loss of potential as a function of time. As seen in frame 405, successful binding of a target molecule to the imprinted polymer blocks the pathway of the electrolyte to the uniform redox probe, resulting in the loss of the redox signal (indication at frame 406).

Figure 5:
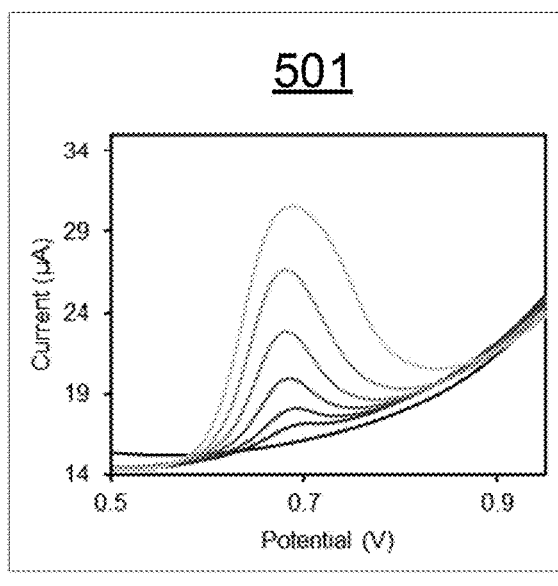
FIG. 5 illustrates, by way of example, target molecule detection and quantification, in accordance with various embodiments of the disclosure.
Figure 5:
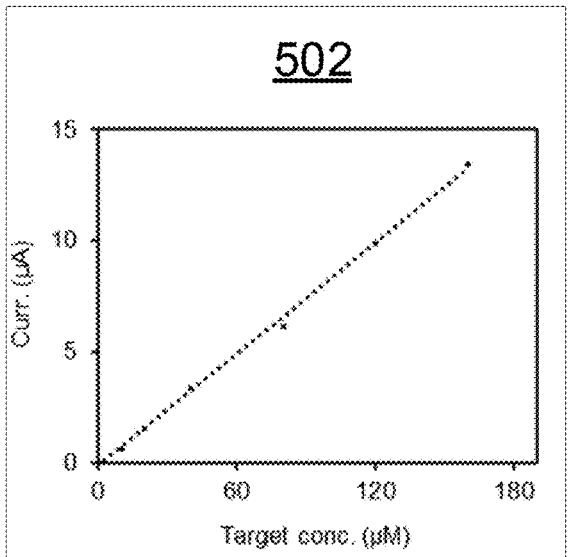
Figure 5:
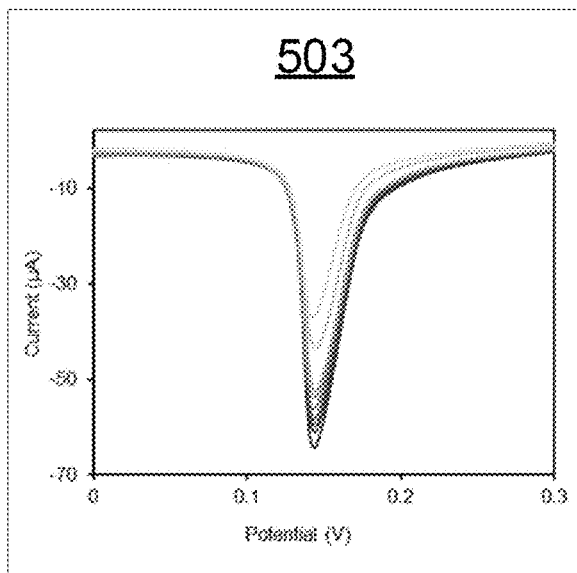
Figure 5:
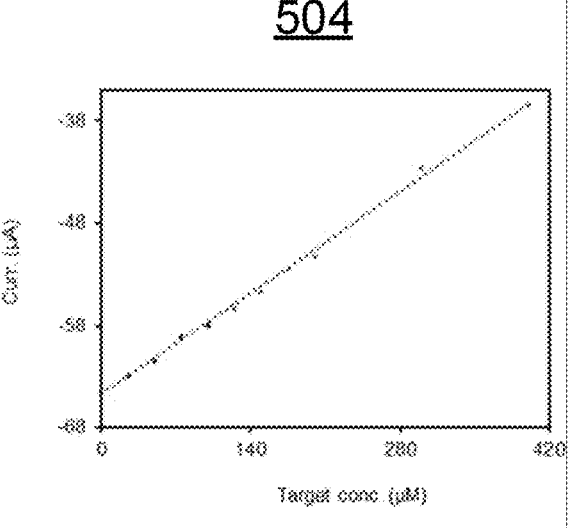

FIG. 5 illustrates, by way of example, detection and quantification of both electroactive target molecules (e.g., frames 501 and 502) and non-electroactive target molecules (e.g., frames 503 and 504) using systems and methods in accordance with various embodiments of the disclosure. Frame 501, for example, depicts detection of an electroactive target molecule, whereas detection of a non-electroactive target molecule is shown in frame 503. Following detection, a calibration curve may be used to determine the quantity or concentration of the target molecule in the biological sample (e.g., frames 502 and 504).

Figure 6:
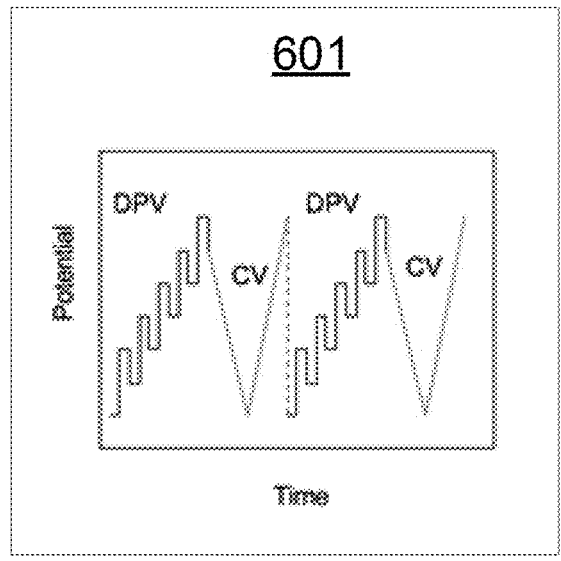
FIG. 6 illustrates examples of continuous detection of the target molecule in accordance with various embodiments of the disclosure.
Figure 6:
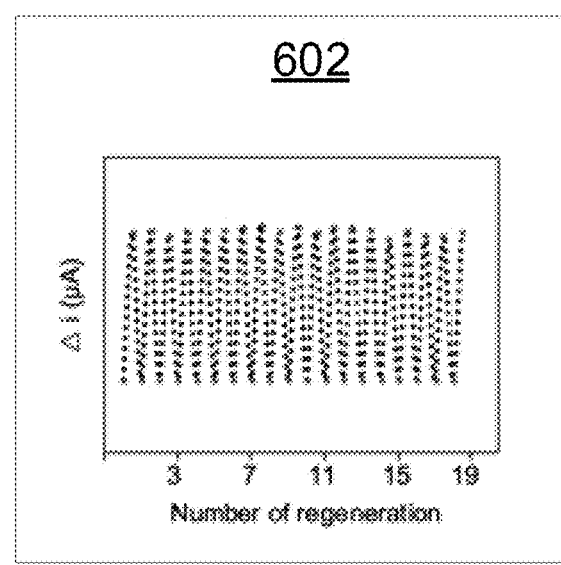
Figure 6:
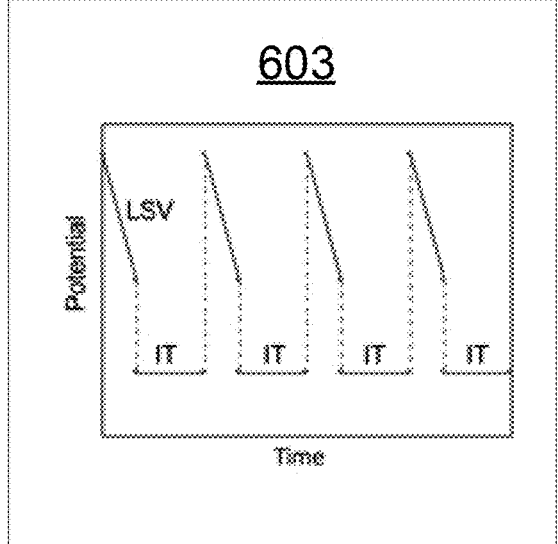
Figure 6:
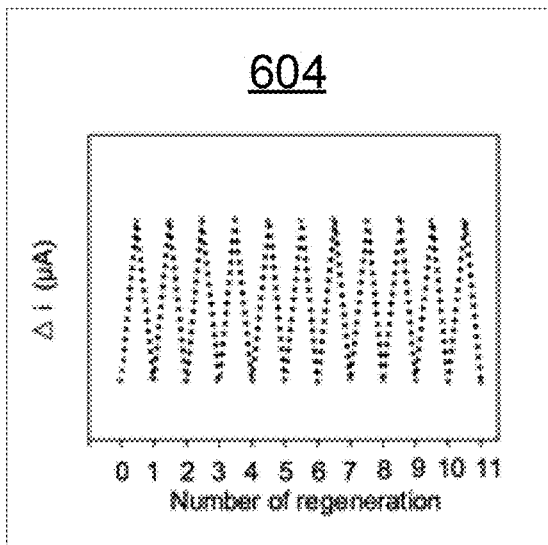

FIG. 6 illustrates, by way of example, continuous detection of both electroactive target molecules (e.g., frames 601 and 602) and non-electroactive target molecules (e.g., frames 603 and 604) using systems and methods in accordance with various embodiments of the disclosure. Frame

601, for example, depicts continuous detection of a target molecule (here, tryptophan) through multiple regenerations of the recognition layer. The corresponding reproducibility of the regeneration/detection approach can be seen in frame 602. Frame 603 depicts continuous detection of a non-electroactive target molecule (here, leucine) through multiple regeneration events using, for example, linear sweep voltammetry (LSV). The corresponding reproducibility of the regeneration/detection approach can be seen in frame 604.

Figure 7:
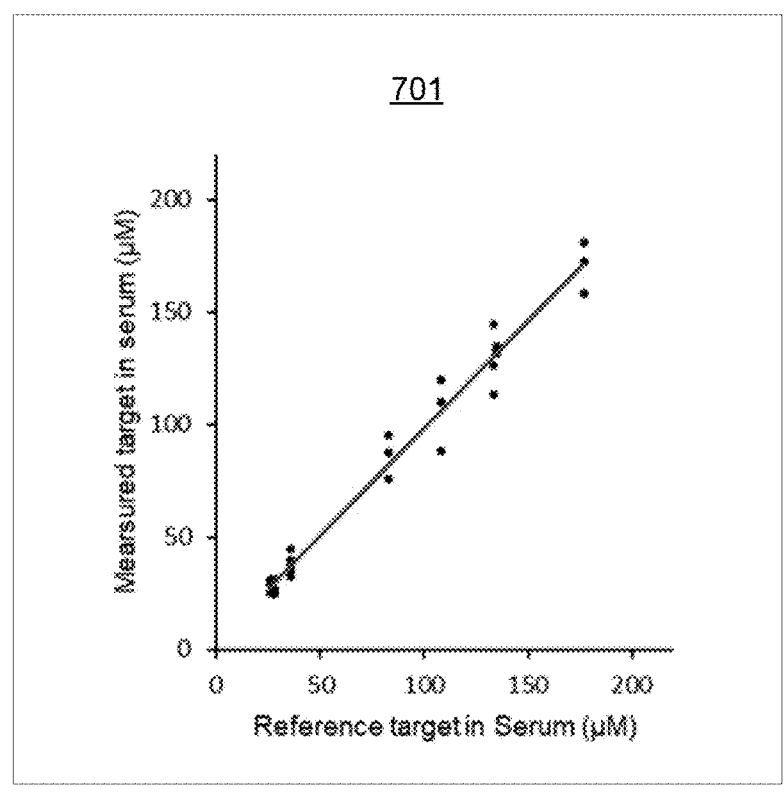
FIG. 7 illustrates, by way of example, detection of a target molecule in a biological sample, in accordance with various embodiments of the disclosure.

FIG. 7 illustrates, by way of example, the accurate detection and quantification of a target molecule in a biological sample using systems and methods according to various embodiments of the disclosure. Frame 701 depicts, for example, biosensor validation for accurately determining the quantity of a target molecule in a serum sample using liquid chromatography/mass spectrometry validation analysis.

By utilizing biosensor 100 in accordance with the technology disclosed herein may be used to detect the presence and/or measure quantity of a target molecule in a biological sample. For example, medical, veterinary, research staff, law enforcement, or other interested personnel can used the disclosed technology to detect the presence and/or measure the quantity of a target molecule in a biological sample. By identifying certain target molecules including, for example, drug metabolites, interested personnel can determine if a subject (e.g., a human, animal, or organism) has taken a certain drug and/or to observe whether a subject is in compliance in taking prescription medications. Embodiments of the technology disclosed herein enable analysis locally at the biosensor without the need for separate equipment, resulting in a less complex system that is smaller and portable. This makes it easier for interested personnel and subjects to view the biosensor data at the device, eliminating the need to utilize other equipment, e.g., enabling field tests for detection of illicit drugs in a subject, or compliance with a drug regiment by the subject. In some embodiments, a portable biosensor may include a built in USB connector, enabling the portable monitoring device to be directly attached to a computer after use to store or review data, or (as discussed above) to charge the portable biosensor.

Figure 8:
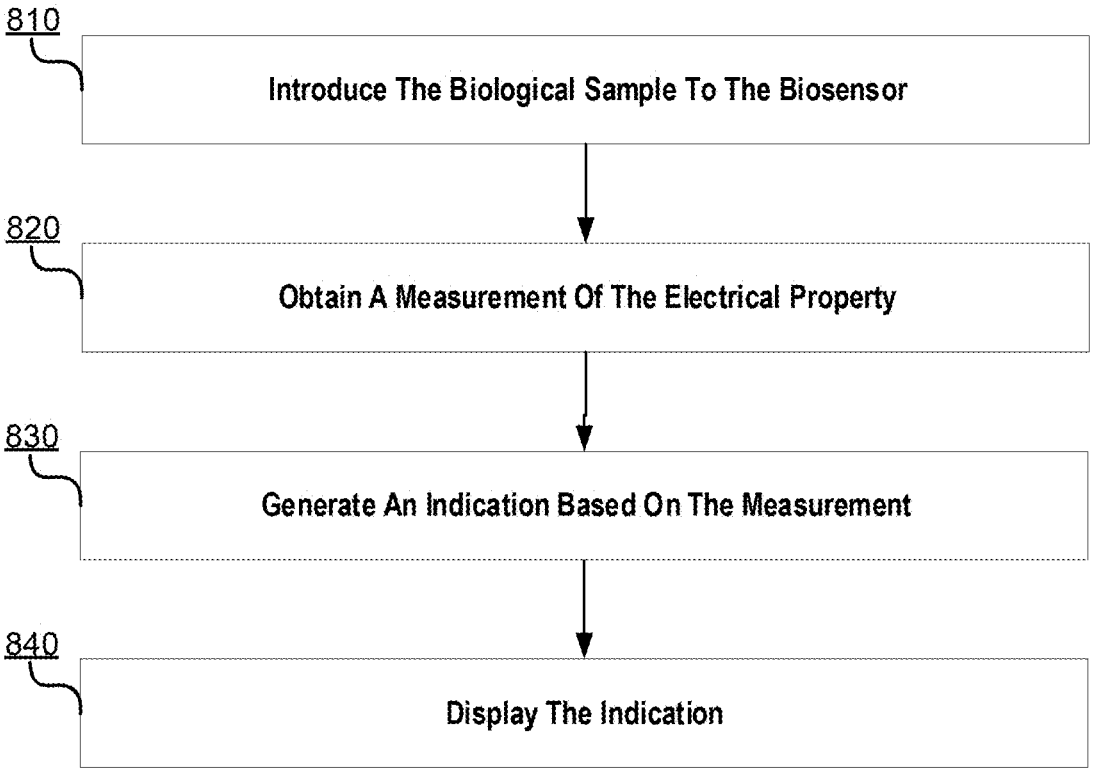
FIG. 8 is an operational flow diagram illustrating an example method for detecting a target molecule in a biological sample, in accordance with implementations of the disclosure.

FIG. 8 is a flow diagram illustrating an example method in accordance with the technology disclosed. At a high level, method 800 may be performed to identify the presence of and quantity of a target molecule in a biological sample using a biosensor. The operations of the various methods described herein are not necessarily limited to the order described or shown in the figures, and one of skill in the art will appreciate, upon studying the present disclosure, variations of the order of the operations described herein that are within the spirit and scope of the disclosure. Let it be appreciated that operations of method 800 may be performed multiple times.

The operations and sub-operations of method 800 may be carried out, in some cases, by and/or using one or more of the components, elements, devices, and sub-components of biosensor 100, as described with respect to at least FIGS. 1-7, as well as components, elements, devices, and sub-components, depicted therein and/or described with respect thereto.

In such instances, the description of method 800 may or may not refer to a corresponding component and/or element, but regardless of whether an explicit reference is made, one of skill in the art will recognize, upon studying the present disclosure, when the corresponding component and/or element may be used. Further, it will be appreciated that such references do not necessarily limit the described methods to the particular component and/or element referred to. Thus, it will be appreciated by one of skill in the art that aspects and features described above in connection with (sub-) components, elements, devices, and components, including variations thereof, may be applied to the various operations described in connection with method 800 without departing from the scope of the present disclosure.

Referring now to FIG. 8, method 800 may be used for detecting a target molecule in a biological sample using biosensor 100, in accordance with implementations of the disclosure. At operation 810, a biological sample that may include a target molecule is introduced to biosensor 100. In embodiments, the biological sample may be introduced to biosensor 100 by depositing the biological sample onto recognition layer 110, such that the target molecule within the biological sample, can form-fit and bind to the imprinted polymer of recognition layer 110. Non-limiting ways the biological sample may be deposited onto the recognition surface of the biosensor include through pipetting, syringe injection, column feeding, micro-pumping, and various machine-automated methods.

Several different biological samples including, for example, blood, sweat, tears, urine, saliva, and/or breath condensation (e.g., condensed vapor) may be introduced to the biosensor in order to detect a target molecule. In embodiments, the target molecule of the biological sample may include an electroactive target molecule. In some embodiments, the target molecule of the biological sample may include a non-electroactive target molecule. In some embodiments, more than one target molecule may be in the biological sample and introduced to the biosensor. In embodiments, the target molecule may include electroactive and/or non-electroactive target molecules.

At operation 820, electrode 120 of biosensor 100 may obtain a measurement of the electrical property of a recognition layer upon the successful binding of a target molecule to the imprinted polymer of recognition layer 110, in accordance with various embodiments of the disclosure. In embodiments, following the binding of the target molecule to the imprinted polymer, electrode 120, electrically coupled to recognition layer 110, may detect a measurement of an electrical property of recognition layer 110. In embodiments, detection of an electrical property with electrode 120 may include binding of an electroactive target molecule to the imprinted polymer of recognition layer 110, wherein an electrolyte of the electroactive target molecule may pass from the target molecule to electrode 120. In some embodiments, detection of an electrical property with electrode 120 may include binding of a non-electroactive target molecule to the imprinted polymer of recognition layer 110, wherein the interaction of the target molecule with the imprinted polymer of recognition layer 110 may block the pathway of the electrolyte to uniform redox probe 150, resulting in the reduction in the redox signal (e.g., frame 406). In embodiments, the electrical property detected by electrode 120 may include an electrical current. In some embodiments, the electrical property may include an electrical voltage. In some embodiments, the electrical property may include an electrical impedance. In some embodiments, the electrical property may include one or more of an electrical current, voltage, and/or impedance. In embodiments, a measurement of an electrical property may include reaching or meeting a threshold of an electrical property. In some embodiments, a measurement of an electrical property may include reaching or meeting a threshold on an electrical property such that when the threshold is reached or met, the measurement may be recorded and sent to the logic circuit for processing. In embodiments, a measurement may include a change in the electrical property. In some embodiments, a measurement may include a change in the electrical property such that when the change in electrical property is detected, for example, from a baseline, the measurement may be sent to the logic circuit for processing. In some embodiments, a change in electrical property may include an increase or decrease in the electrical property from a certain baseline.

In embodiments, more than one measurement of an electrical property may be obtained by sweeping electrode 120 such that the imprinted polymers of recognition layer 110 may be regenerated during a reading. In some embodiments, sweeping electrode 120 allows for continuous detection of a measurement of an electrical property. In some embodiments, sweeping electrode 120 may allow for continuous detection of more than one measurement of an electrical property. Sweeping electrode 120 may include rapid voltammetric and/or amperometric sweeping.

Referring still to FIG. 8, at operation 830, logic circuit 130 may generate an indication that the target molecule is present in the biological sample, in accordance with embodiments of the disclosure. In embodiments, logic circuit 130 may include a processor and a non-transitory memory with computer executable instructions embedded thereon. In embodiments, electrode 120 may be electrically coupled to logic circuit 130, and upon the successful binding of a molecular target to an imprinted polymer of recognition layer 110, the computer executable instructions cause the processor to identify the electrical property detected with electrode 120. In some embodiments, the computer executable instructions cause the processor to generate an indication identifying the presence of the target molecule based on the electrical property of recognition layer 110 detected with electrode 120. The indication generated may be identified visually by a display and/or LED(s), or through other means of sensory communication including auditory cues.

In various embodiments, at operation 840, logic circuit 130 may output the indication identifying the presence of the target molecule to display 140 in accordance with various embodiments of the disclosure. In embodiments, upon the binding of a target molecule to the imprinted polymer of the recognition layer 110 and detection of the measurement of an electrical property with electrode 120, the computer executable instructions of logic circuit 130 further cause the processor to output the indication identifying the presence of the target molecule to display 140. In embodiments, display 140 may display visually the indication identifying the presence of the target molecule. In some embodiments, the display may include an LCD screen. In some embodiments, the indication displayed may include a visual representation of the measurement of the electrical property, including, for example, an electrical current and/or an electrical voltage. In some embodiments, the indication displayed may include a visual representation of the measurement of the electrical property, including for example, a change in the electrical current and/or voltage (e.g., frames 306, 406, 501, and 503). In some embodiments, the indication displayed may include a visual representation of the measurement of the electrical property, including for example, a change in the electrical impedance. In some embodiments, the visual representation may include, for example, a graph having an x and y-axis. In some embodiments, the indication may include a quantification of the amount of target molecule present in the biological sample. In some embodiments, the quantification of target molecule present in a biological sample may include units of potential (e.g., voltage or "V"), current (e.g., amps or "A"), and/or impedance (e.g., ohms or "Z"). In some embodiments, various amounts of each of these units may include nano-units, mirco-units, mili-units, and/or liter-units.

Figure 9:
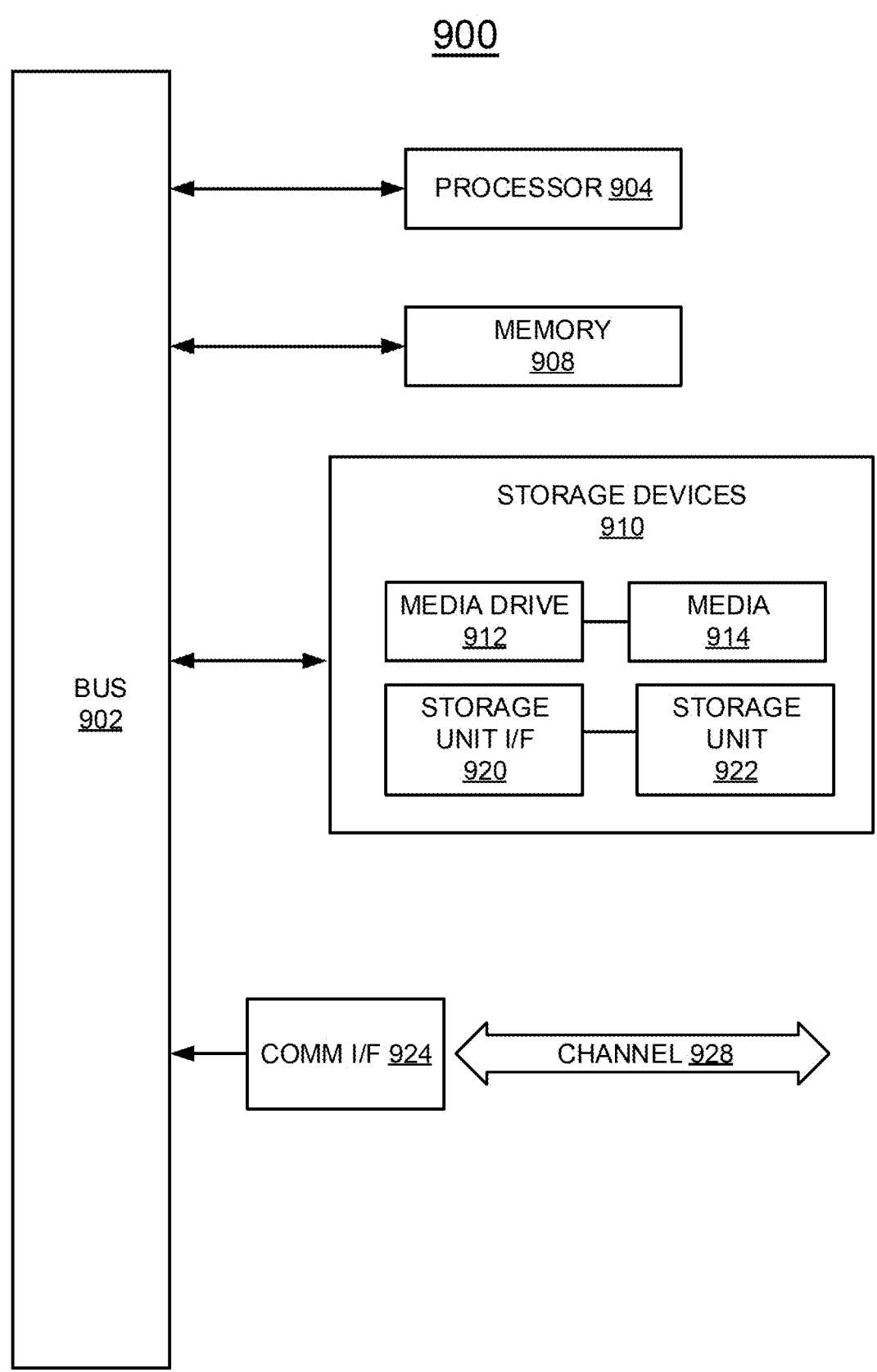
FIG. 9 illustrates a computer component that can be utilized in implementing architectures and methods, in accordance with various implementations of the disclosure.

FIG. 9 illustrates example computing component 900, which may in some instances include a processor/controller resident on a computer system (e.g., biosensor 100). Computing component 900 may be used to implement various features and/or functionality of embodiments of the systems, devices, and methods disclosed herein. With regard to the above-described embodiments set forth herein in the context of systems, devices, and methods described with reference to FIGS. 1 through 8, including embodiments involving biosensor 100, one of skill in the art will appreciate additional variations and details regarding the functionality of these embodiments that may be carried out by computing component 900. In this connection, it will also be appreciated by one of skill in the art upon studying the present disclosure that features and aspects of the various embodiments (e.g., systems) described herein may be implemented with respected to other embodiments (e.g., methods) described herein without departing from the spirit of the disclosure.

As used herein, the term component may describe a given unit of functionality that may be performed in accordance with one or more embodiments of the present application. As used herein, a component reference a module, and/or may be implemented utilizing any form of hardware, software, or a combination thereof. For example, one or more processors, controllers, ASICs, PLAs, PALs, CPLDs, FPGAs, logical components, software routines or other mechanisms may be implemented to make up a component. In embodiment, the various components described herein may be implemented as discrete components or the functions and features described may be shared in part or in total among one or more components. In other words, as would be apparent to one of ordinary skill in the art after reading this description, the various features and functionality described herein may be implemented in any given application and may be implemented in one or more separate or shared components in various combinations and permutations. Even though various features or elements of functionality may be individually described or claimed as separate components, one of ordinary skill in the art will understand upon studying the present disclosure that these features and functionality may be shared among one or more common software and hardware elements, and such description shall not require or imply that separate hardware or software components are used to implement such features or functionality.

Where components of the application are implemented in whole or in part using software, in one embodiment, these software elements can be implemented to operate with a computing or processing component capable of carrying out the functionality described with respect thereto. One such example computing component is shown in FIG. 9. Various embodiments are described in terms of this example-computing component 900. After reading this description, it will become apparent to a person skilled in the relevant art how to implement the application using other computing components or architectures.

Referring now to FIG. 9, computing component 900 may represent, for example, computing or processing capabilities found within a self-adjusting display, desktop, laptop, note-book, and tablet computers; hand-held computing devices (tablets, PDA's, smart phones, cell phones, palmtops, etc.); workstations or other devices with displays; servers; or any other type of special-purpose or general-purpose computing devices as may be desirable or appropriate for a given application or environment. Computing component 900 might also represent computing capabilities embedded within or otherwise available to a given device. For example, a computing component might be found in other electronic devices such as, for example navigation systems, portable computing devices, and other electronic devices that might include some form of processing capability.

Computing component 900 might include, for example, one or more processors, controllers, control components, or other processing devices, such as a processor 904. Processor 904 might be implemented using a general-purpose or special-purpose processing engine such as, for example, a microprocessor, controller, or other control logic. In the illustrated example, processor 904 is connected to a bus 902, although any communication medium can be used to facilitate interaction with other components of computing component 900 or to communicate externally.

Computing component 900 might also include one or more memory components, simply referred to herein as main memory 908. For example, preferably random access memory (RAM) or other static or dynamic memory, might be used for storing information and instructions to be executed by processor 904. Main memory 908 might also be used for storing temporary variables or other intermediate information during execution of instructions to be executed by processor 904. Computing component 900 might likewise include a read only memory ("ROM") or other static storage device coupled to bus 902 for storing static information and instructions for processor 904.

The computing component 900 might also include one or more various forms of information storage mechanism 910, which might include, for example, a media drive 912 and a storage unit interface 920. The media drive 912 might include a drive or other mechanism to support fixed or removable storage media 914. For example, a hard disk drive, a solid state drive, a magnetic tape drive, an optical disk drive, a compact disc (CD) or digital video disc (DVD) drive (R or RW), or other removable or fixed media drive might be provided. Accordingly, storage media 914 might include, for example, a hard disk, an integrated circuit assembly, magnetic tape, cartridge, optical disk, a CD or DVD, or other fixed or removable medium that is read by, written to or accessed by media drive 912. As these examples illustrate, the storage media 914 can include a computer usable storage medium having stored therein computer software or data.

In alternative embodiments, information storage mechanism 910 might include other similar instrumentalities for allowing computer programs or other instructions or data to be loaded into computing component 900. Such instrumentalities might include, for example, a fixed or removable storage unit 922 and an interface 920. Examples of such storage units 922 and interfaces 920 can include a program cartridge and cartridge interface, a removable memory (for example, a flash memory or other removable memory component) and memory slot, a PCMCIA slot and card, and other fixed or removable storage units 922 and interfaces 920 that allow software and data to be transferred from the storage unit 922 to computing component 900.

Computing component 900 might also include a communications interface 924. Communications interface 924 might be used to allow software and data to be transferred between computing component 900 and external devices. Examples of communications interface 924 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 924 might typically be carried on signals, which can be electronic, electromagnetic (which includes optical) or other signals capable of being exchanged by a given communications interface 924. These signals might be provided to communications interface 924 via a channel 928. This channel 928 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 908, storage unit 920, media 914, and channel 928. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 900 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The details of some embodiments of the systems and methods of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

What is claimed is:

1. A method for detecting a target molecule in a biological sample comprising an excreted bodily fluid selected from sweat, blood, urine, saliva, or tears, using a biosensor comprised of a recognition layer with at least one imprinted polymer comprising an electropolymerized polyphenol formed as an insulating film, the imprinted polymer being shaped to have a profile that substantially matches a profile of the target molecule, an electrode electrically coupled to the recognition layer, the electrode comprising a graphene substrate, and a logic circuit, the method comprising:

introducing the biological sample by depositing the excreted bodily fluid onto the recognition layer of the biosensor, wherein the target molecule will form-fit and bind to the imprinted polymer when the target molecule is present in the deposited biological sample;

obtaining, with the electrode, a measurement of an electrical property of the recognition layer; and generating, with the logic circuit, an indication that the target molecule is present in the biological sample based on the measurement of the electrical property.

2. The method of claim 1, further comprising sweeping the electrode to regenerate the recognition layer in-situ.

3. The method of claim 1, wherein the electrical property is an electrical current.

4. The method of claim 1, wherein the electrical property is an electrical voltage.

5. The method of claim 1, wherein the electrical property is an electrical impedance.

6. The method of claim 1, wherein the target molecule further comprises an electroactive molecule.

7. The method of claim 6, wherein the electroactive molecule is tryptophan, tyrosine, phenylalanine, dopamine, vitamin C, vitamin B6, vitamin B12, uric acid, mycophenolic acid, caffeine, methionine, cortisol, noradrenaline, or adrenaline.

8. The method of claim 1, further comprising depositing a uniform redox probe on a surface of the electrode.

9. The method of claim 1, wherein the target molecule further comprises a non-electroactive molecule.

10. The method of claim 9, wherein the target molecule is leucine, iso-leucine, valine, busulfan, cyclophosphamide, creatinine, or urea.

11. A method for detecting a target molecule in a biological sample comprising an excreted bodily fluid selected from sweat, blood, urine, saliva, or tears, using a biosensor comprised of a recognition layer with at least one imprinted polymer, the imprinted polymer being an electropolymerized polymer and shaped to have a profile that substantially matches a profile of the target molecule, an electrode electrically coupled to the polymer layer and having at least one surface with an uniform redox probe, the electrode further comprising a graphene substrate, a logic circuit, and a display, the method comprising:

introducing the biological sample by depositing the excreted bodily fluid onto the recognition layer of the biosensor, wherein the target molecule will form-fit and bind to the imprinted polymer when the target molecule is present in the deposited biological sample;

obtaining, with the electrode, a measurement of an electrical property of the recognition layer upon the target molecule binding to the imprinted polymer;

generating, with the logic circuit, an indication that the target molecule is present in the deposited biological sample based on the measurement of the electrical property; and causing the display to display the indication identifying the presence of the target molecule.

12. The method of claim 11, further comprising sweeping the electrode to regenerate the recognition layer in-situ.

13. The method of claim 11, wherein the uniform redox probe comprises ferric ferrocyanide.

14. The method of claim 11, wherein the electrical property is an electrical current.

15. The method of claim 11, wherein the electrical property is an electrical voltage.

16. The method of claim 11, wherein the electrical property is an electrical impedance.

17. The method of claim 11, wherein the target molecule further comprises an electroactive molecule.

18. The method of claim 17, wherein the electroactive molecule is tryptophan, tyrosine, phenylalanine, dopamine, vitamin C, vitamin B6, vitamin B12, uric acid, mycophenolic acid, caffeine, methionine, cortisol, noradrenaline, or adrenaline.

19. The method of claim 11, further comprising depositing a uniform redox probe on a surface of the electrode.

20. The method of claim 11, wherein the target molecule further comprises a non-electroactive molecule.

* * * * *